(12) United States Patent
Honda et al.

(10) Patent No.: US 7,264,652 B2
(45) Date of Patent: Sep. 4, 2007

(54) FILTER FOR COLLECTING CHLORINATED ORGANIC COMPOUND

(75) Inventors: Katsuhisa Honda, Matsuyama (JP); Noriaki Hamada, Matsuyama (JP); Hirofumi Nakamura, Matsuyama (JP); Hisaji Matsui, Osaka (JP); Kiyotaka Kobayashi, Osaka (JP)

(73) Assignees: Miura Co., Ltd., Matsuyama (JP); Osaka Gas Co., Ltd., Osaka (JP)

( * ) Notice: Subject to any disclaimer, the term of this patent is extended or adjusted under 35 U.S.C. 154(b) by 312 days.

(21) Appl. No.: 10/511,470

(22) PCT Filed: Jun. 17, 2003

(86) PCT No.: PCT/JP03/07689

§ 371 (c)(1),
(2), (4) Date: Oct. 18, 2004

(87) PCT Pub. No.: WO2004/010110

PCT Pub. Date: Jan. 29, 2004

(65) Prior Publication Data

US 2005/0241481 A1     Nov. 3, 2005

(30) Foreign Application Priority Data

Jul. 19, 2002 (JP) .............................. 2002-210585

(51) Int. Cl.
*B01D 59/26* (2006.01)
(52) U.S. Cl. ........................... 95/132; 95/287; 96/134; 96/154; 55/486; 55/523; 55/527; 55/DIG. 5; 210/488; 210/489; 210/490; 210/505; 264/628; 264/DIG. 48

(58) Field of Classification Search .................. 95/273, 95/82, 87, 88, 90, 116, 132, 141, 143, 274, 95/285, 142, 286; 96/101, 105, 106, 143–146, 96/422, 413, 134, 154; 55/527, 486; 210/503, 210/504, 506, 508, 505, 507
See application file for complete search history.

(56) References Cited

U.S. PATENT DOCUMENTS 3,505,794 A * 4/1970 Nutter et al. ................. 55/487

(Continued)

FOREIGN PATENT DOCUMENTS

EP          1219335 A    7/2002

(Continued)

OTHER PUBLICATIONS

Japanese Industrial Standard/JIS K 0311 Method for determination of tetra through octa- chlorodibenzo-p-dioxins, tetra- through octa-chlorodibenzofurans and coplanar polychlorobiphenuls in stationary source emmissions, pp. 1-62, (1999).

(Continued)

*Primary Examiner*—Duane Smith
*Assistant Examiner*—Robert Clemente
(74) *Attorney, Agent, or Firm*—Birch, Stewart, Kolasch & Birch, LLP

(57) ABSTRACT

The collecting filter can capture and collect various chlorinated organic compounds in both particulate form and gaseous form contained in a fluid at the same time, and is easy to extract the collected chlorinated organic compounds therefrom. This collecting filter 7 is provided with a fluid-permeable molded body containing fibers and an inorganic binder for binding the fibers to one another, and a hydrophobic material having higher hydrophobicity than that of the fibers and the inorganic binder, which is retained in the molded body. Various chlorinated organic compounds such as dioxins in both particulate form and gaseous form contained in the sample gas are captured and collected upon passage through the collecting filter 7.

18 Claims, 8 Drawing Sheets

U.S. PATENT DOCUMENTS

| | | | | |
|---|---|---|---|---|
| 3,891,417 | A | * | 6/1975 | Wade ........................ 96/117.5 |
| 4,217,386 | A | * | 8/1980 | Arons et al. ................ 428/198 |
| 4,889,630 | A | * | 12/1989 | Reinhardt et al. .......... 210/490 |
| 4,968,467 | A | * | 11/1990 | Zievers ....................... 264/621 |
| 5,106,395 | A | * | 4/1992 | Weber et al. ................. 95/279 |
| 5,895,520 | A | * | 4/1999 | Rolke et al. .................. 95/132 |
| 6,203,762 | B1 | * | 3/2001 | Skalla et al. ................ 422/171 |
| 6,555,385 | B1 | | 4/2003 | Honda et al. |
| 2003/0089092 | A1 | * | 5/2003 | Bause et al. ................. 55/524 |

FOREIGN PATENT DOCUMENTS

| | | | |
|---|---|---|---|
| EP | 1219335 A1 | * | 7/2002 |
| JP | 2001-4501 A | | 1/2001 |
| JP | 2001004501 A | * | 1/2001 |
| JP | 2001-269521 A | | 10/2001 |
| JP | 2001-349810 A | | 12/2001 |
| WO | WO 099/37987 A1 | | 7/1999 |

OTHER PUBLICATIONS

"Method 23" formulated by the U.S. Environmental Protection Agency (EPA), as Appendix A, pp. 8-42, of 40 C.F.R. 60.

British Standard "Stationary source emissions—Determination of the mass concentration of PCDDs/PCDFs" Part 1, 2 and 3, The European Standard EN 1948-1:1997.

* cited by examiner

FILTER FOR COLLECTING CHLORINATED ORGANIC COMPOUND

TECHNICAL FIELD

The present invention relates to a collecting filter, in particular, a filter for collecting a chlorinated organic compound.

BACKGROUND ART

An exhaust gas generated from incineration facilities for incinerating wastes such as industrial wastes and general home garbage contains various chlorinated organic compounds such as dioxins, polychlorobiphenyls, chlorophenol and chlorobenzene.

Herein, the word, dioxins, is a general term of polychlorodibenzo-para-dioxins (PCDDs), polychlorodibenzofurans (PCDFs) and the like, and is an environmental pollutant which is extremely toxic, as well known. Inter alia, 2,3,7,8-tetrachlorodibenzo-para-dioxin ($T_4CDD$) is known as a most toxic substance. In addition, polychlorobiphenyls are similarly an environmental pollutant which is considerably toxic. Inter alia, coplanar polychlorobiphenyls (Co-PCBs) are recognized as a most toxic substance like dioxins. In the present application, the word "dioxins" is used to include coplanar polychlorobiphenyls (Co-PCBs) in addition to polychlorodibenzo-para-dioxins (PCDDs) and polychlorodibenzofurans (PCDFs) according to Article 2 of "Law Concerning Special Measures against Dioxins" established in 1999 as Law No.105 in Japan.

On the other hand, although chlorinated organic compounds such as chlorophenol and chlorobenzene are less toxic as compared with dioxins, it has been found that they are easily converted into dioxins under certain conditions, for example, using various elements contained in fly ashes as catalyst in an incinerator in a temperature range of an exhaust gas. Therefore, they are recognized as environmental pollutants like dioxins. For this reason, from a viewpoint of environmental protection, it becomes an urgent issue to establish a countermeasure for removing the aforementioned various chlorinated organic compounds from a fluid such as an exhaust gas and waste-water. At the same time, it is also urgent in global scale to establish a procedure for analyzing chlorinated organic compounds contained in such a fluid.

Meanwhile, when chlorinated organic compounds contained in a fluid are analyzed, first, it is necessary to obtain a sample precisely and exactly from a fluid to be analyzed. For example, when chlorinated organic compounds contained in an exhaust gas are analyzed, it is necessary to collect a prescribed amount of a sample gas from a space containing the exhaust gas, for example, a flue through which the exhaust gas is flown, and assuredly capture all various chlorinated organic compounds contained in this sample gas without leakage. In particular, the aforementioned dioxins, which are environmental pollutants, are contained in the sample gas at an extremely small amount, and dioxins are in various forms such as particulate form and gaseous form, and there are many kinds of dioxins. Therefore, without precise collection of them, analysis results having high reliance cannot be expected. Further, since there is a possibility that coplanar polychlorobiphenyl is contained in the atmospheric air at a large amount, when a sample gas is contaminated with the air containing coplanar polychlorobiphenyl, analysis results having high reliance cannot be expected similarly. For this reason, in order to guarantee the accuracy of the analysis results, Japan, US and each country of Europe respectively have been officially establishing a method, for example, for collecting a necessary sample for analyzing a chlorinated organic compound such as dioxins contained in an exhaust gas.

For example, Japanese Industrial Standard JIS K 0311:1999 established on Sep. 20, 1999 stipulates "Method for determination of tetra- through octa-chlorodibenzo-p-dioxins, tetra- through octa-chlorodibenzofurans and coplanar polychlorobiphenyls in stationary source emissions", and specifically exemplifies a device for collecting a sample gas including a chlorinated organic compound such as dioxins therein. This collecting device is provided mainly with a collecting tube for collecting a sample gas from a flue of an incineration equipment through which an exhaust gas is flown, a first captor provided with a filter material for capturing a chlorinated organic compound mainly in a particulate form contained in the sample gas collected by the collecting tube, and a second captor for capturing a chlorinated organic compound in a gaseous form which is hardly captured by the first captor. Herein, the second captor is provided mainly with a liquid capturing portion composed of a plurality of glass impingers containing an absorbent liquid and an adsorptive capturing portion arranged with an adsorbent (e.g. styrene-divinylbenzene copolymer sold under trade name of XAD-2), and is constructed that a chlorinated organic compound in a gaseous form which is not captured by the first captor can be captured by the absorbent liquid contained in the impingers and the adsorbent.

Since such a collecting device has a complicated construction provided with the first captor and the second captor, and is expensive because of use of many glass instruments, the device is utilized repeatedly in many cases. In this case, since it is required to keep the respective members such as impingers clean in order to retain the reliance of measurement data, a preparatory work such as washing procedure before collection of a sample gas becomes very troublesome. In addition, upon capturing of a chlorinated organic compound in a gaseous form contained in a sample gas by the second captor, it is necessary to cool the second captor using a coolant such as dry ice, and the procedure of collecting a sample itself becomes very complicated. Further, after collection of a sample gas, it is necessary to extract a chlorinated organic compound captured by the first captor and the second captor. Herein, since it is necessary to extract individually the chlorinated organic compounds captured by the first captor and the second captor having a complicated construction, respectively, the extraction procedure itself is troublesome, and it takes a long time until completion. In addition, the reliance of analysis results depends on skill of extraction procedure in many cases. Further, since this collecting device is composed of two types of captors of the first captor and the second captor, the device is inevitably scaled up. Moreover, since the device uses many glass instruments and therefore is easily damaged, handling at sample gas collection and conveyance are also difficult.

On the other hand, Environmental Protection Agency (EPA) of USA and European Committee for Standardization (CEN) also stipulate their own official methods. However, collecting devices shown therein are different from the aforementioned Japanese device in details, but are slightly different in respect of complicated construction and difficult handling.

The object of the present invention is to simultaneously capture and collect various kinds of chlorinated organic compounds in both particulate form and gaseous form contained in a fluid, and easily extract the collected chlorinated organic compounds.

DISCLOSURE OF THE INVENTION

A filter for collecting chlorinated organic compound of the present invention is for selecting and collecting a chlorinated organic compound contained in a fluid from the fluid. The filter comprises a fluid-permeable molded body containing fibers and an inorganic binder for binding the fibers to one another, and a hydrophobic material having higher hydrophobicity than that of the fibers and the inorganic binder, which is retained in the molded body.

Since the filter for collecting chlorinated organic compound of the present invention is such that a hydrophobic material is retained in a fluid-permeable molded body, a fluid containing various chlorinated organic compounds such as dioxins in both particulate form and gaseous form can pass through the filter. Thereupon, the aforementioned various chlorinated organic compounds in both forms contained in the fluid are captured simultaneously by the fibers and the inorganic binder contained in the molded body as well as the hydrophobic material retained in a molded body, and accordingly are selected from the fluid. That is, chlorinated organic compounds in both particulate form and gaseous form contained in the fluid are collected by the collecting filter. Collected chlorinated organic compounds can be extracted by applying various extracting procedures to the collecting filter.

The fibers used in this collecting filter are, for example, at least one kind of fibers selected from the group consisting of glass fiber, alumina fiber and silica fiber. It is preferable that an average aspect ratio of the fibers is usually 1,000 to 10,000.

The inorganic binder used in this collecting filter has an adsorbing capability, for example, to a chlorinated organic compound. It is preferable that the inorganic binder has an adsorbing capability, for example, to a tar. The inorganic binder used herein is, for example, at least one kind of compounds selected from the group consisting of alumina, zeolite and silicon dioxide. In addition, the inorganic binder is usually particulate.

Further, it is preferable that the hydrophobic material used in this collecting filter has an adsorbing capability to a chlorinated organic compound. The hydrophobic material is, for example, at least one kind of materials selected from the group consisting of activated carbon, graphite and styrene-divinylbenzene copolymer.

The molded body constituting this collecting filter has usually a bulk density of 0.1 to 1 $g/cm^3$. In this collecting filter, the hydrophobic material is usually retained at 0.01 to 10.0% by weight of the molded body.

A preferable embodiment of this collecting filter is, for example, such that the fibers are activated alumina fibers, the inorganic binder is particulate activated alumina, and the hydrophobic material is powdery activated carbon. In this embodiment, a bulk density of the molded body is preferably, for example, 0.3 to 0.7 $g/cm^3$.

The collecting filter of the present invention is formed into, for example, a cylinder having one closed end.

A process of the present invention is a process for preparing a filter for selecting and collecting a chlorinated organic compound contained in a fluid from the fluid. The process comprises a step of preparing a molding material containing fibers and an inorganic binder for binding the fibers to one another, a step of molding the molding material into a predetermined shape and sintering this to obtain a molded body, and a step of making the molded body retain a hydrophobic material having higher hydrophobicity than that of the fibers and the inorganic binder.

In such a process for producing the filter, since the aforementioned molding material is molded and thereafter sintered, a molded body having fluid permeability can be prepared. Since this molded body contains the fibers and the inorganic binder, and retains the hydrophobic material having higher hydrophobicity than that of the fibers and the inorganic binder, when a fluid containing various chlorinated organic compounds such as dioxins in both particulate form and gaseous form passes therethrough, the molded body can capture the chlorinated organic compounds and select them from the fluid. In addition, the chlorinated organic compounds in both particulate form and gaseous form collected by this molded body can be easily extracted by applying various extracting methods to the molded body.

In one embodiment of this process, for example, at least one of the elements including the fibers and the inorganic binder is alumina, and a temperature at sintering is set at 150 to 170° C.

Also, this process further comprises a step of immersing the molded body in an aqueous dispersion of the inorganic binder and then drying the molded body, before the step of making the molded body retain the hydrophobic material.

A collector of the present invention is for collecting a chlorinated organic compound contained in a fluid which is flown in a transportation tube, and is provided with a filter having fluid permeability for passing the fluid from the transportation tube therethrough, and a container which accommodates the filter and has an outlet for discharging the fluid which has passed through the filter to the outside. Herein, the filter is provided with a molded body containing fibers and an inorganic binder for binding the fibers to one another, and a hydrophobic material which is retained in the molded body and has higher hydrophobicity than that of the fibers and the inorganic binder.

In the collector of the present invention, a fluid from the transportation tube is passed through the filter in the container and, thereafter, discharged through the outlet to the outside. Thereupon, various chlorinated organic compounds such as dioxins in both particulate form and gaseous form contained in the fluid are captured simultaneously by the fibers and the inorganic binder constituting the molded body as well as the hydrophobic material retained in the molded body, selected from the fluid, and collected by the filter. The various chlorinated organic compounds collected by the filter can be easily extracted by applying various extracting procedures to the filter.

In this collector, the filter is, for example, a cylinder having an opening for inserting the transportation tube into one side and closed in the other side.

A method of the present invention is a method for collecting chlorinated organic compound contained in a fluid flowing in a transportation tube. The method comprises a step of passing the fluid from the transportation tube through a filter provided with a fluid-permeable molded body containing fibers and an inorganic binder for binding the fibers to one another, and a hydrophobic material having higher hydrophobicity than that of the fibers and the inorganic binder, which is retained in the molded body.

Since such a method for collecting chlorinated organic compound uses the filter provided with the aforementioned molded body containing the fibers and the inorganic binder and the hydrophobic material retained in this molded body, when the fluid from the transportation tube passes through the filter, various chlorinated organic compounds such as dioxins in both particulate form and gaseous form contained therein are captured and collected by the filter at the same time. The various chlorinated organic compounds collected by the filter can be easily extracted by applying various extracting procedures to the filter.

Other objects and effects of the present invention will be described in the following detailed explanation.

BEST MODE FOR CARRYING OUT THE INVENTION

Figure 1:
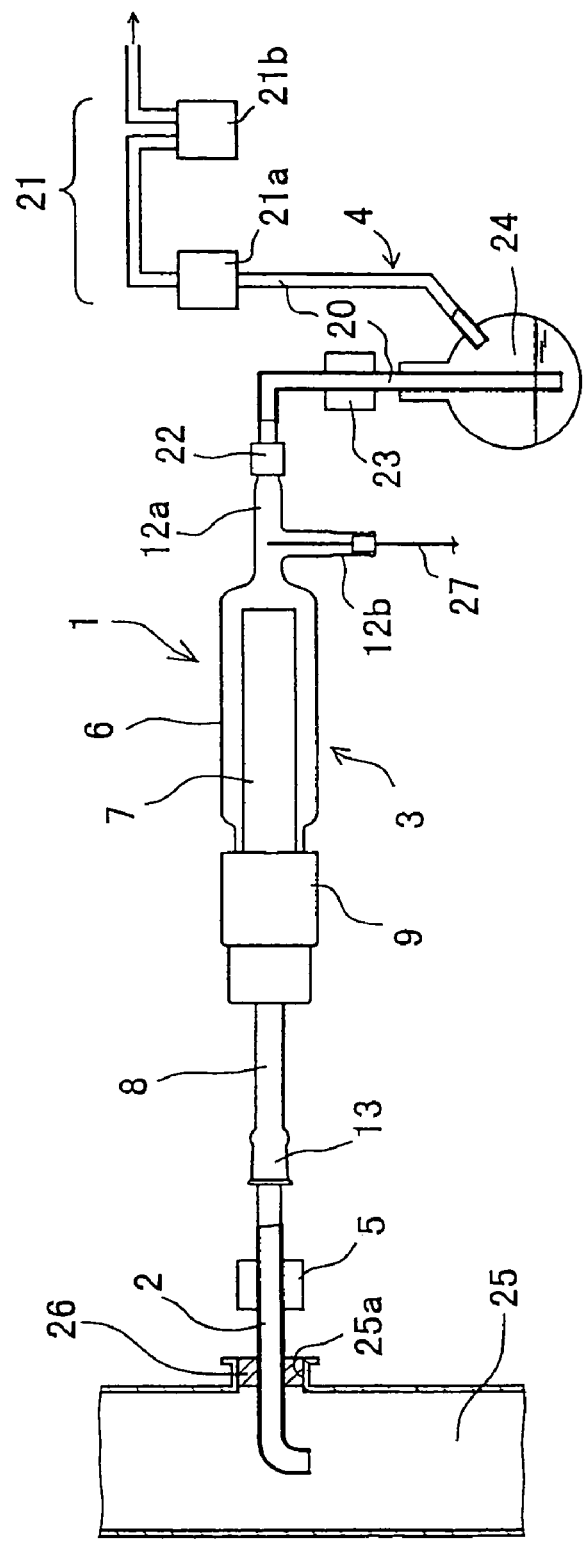
FIG. 1 is a brief construction view of an apparatus for collecting chlorinated organic compound in which the collector in accordance with one embodiment of the present invention is adopted.

FIG. 1 shows a brief construction of an apparatus for collecting chlorinated organic compound in which one embodiment of collector of chlorinated organic compound according to the present invention is adopted. This collecting apparatus 1 is for collecting a chlorinated organic compound contained in a sample fluid (sample gas) such as an exhaust gas, among a fluid. In the figure, the collecting apparatus 1 is provided mainly with a collecting tube 2, a collector 3 (one embodiment of collector according to the present invention) and an aspirator 4.

The collecting tube 2 is made of, for example, a borosilicate glass or a transparent quartz glass, and has a cooling device 5 for cooling the sample gas which passes through the interior thereof.

Figure 2:
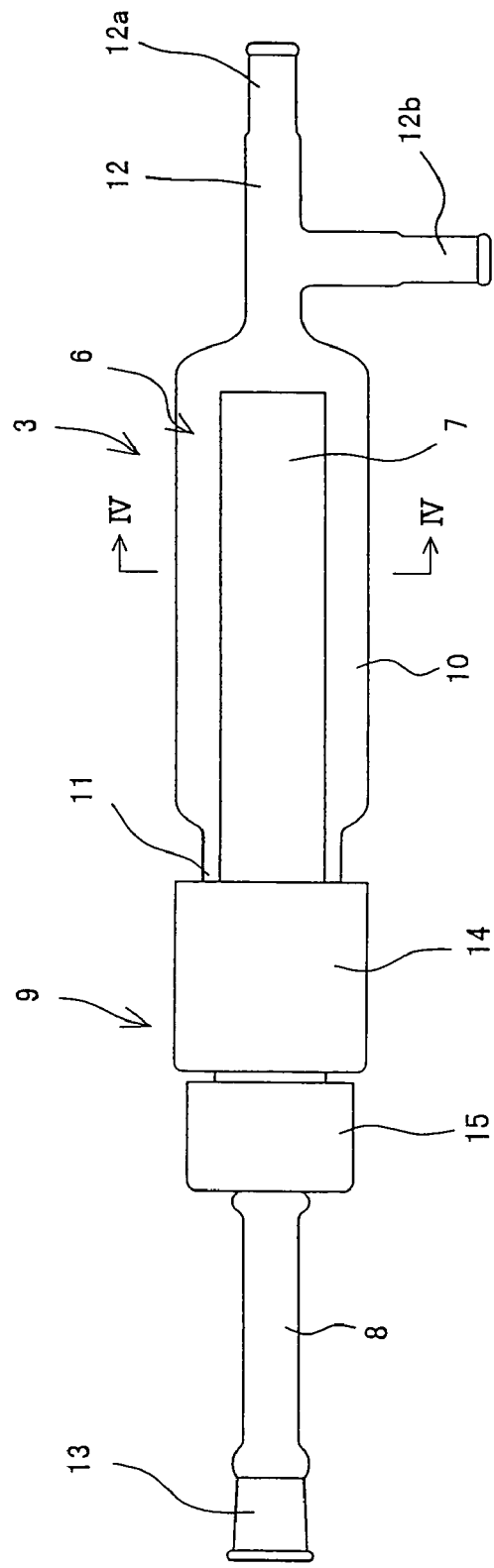
FIG. 2 is a front view of the collector.
Figure 3:
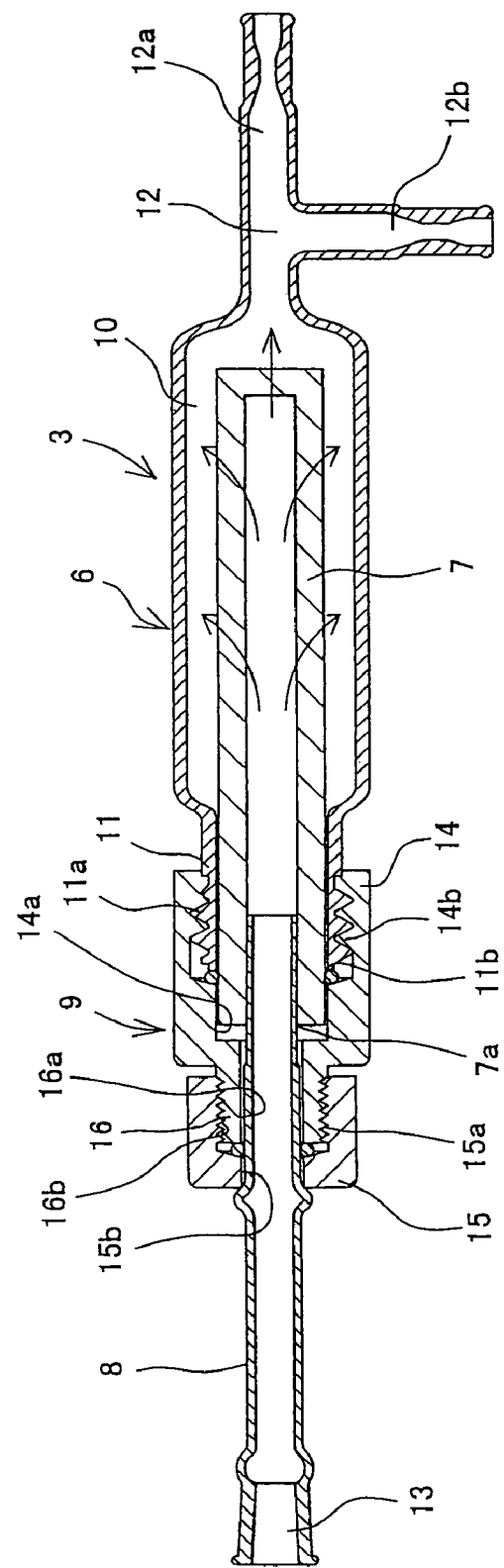
FIG. 3 is a longitudinal cross-sectional view of the collector.
Figure 4:
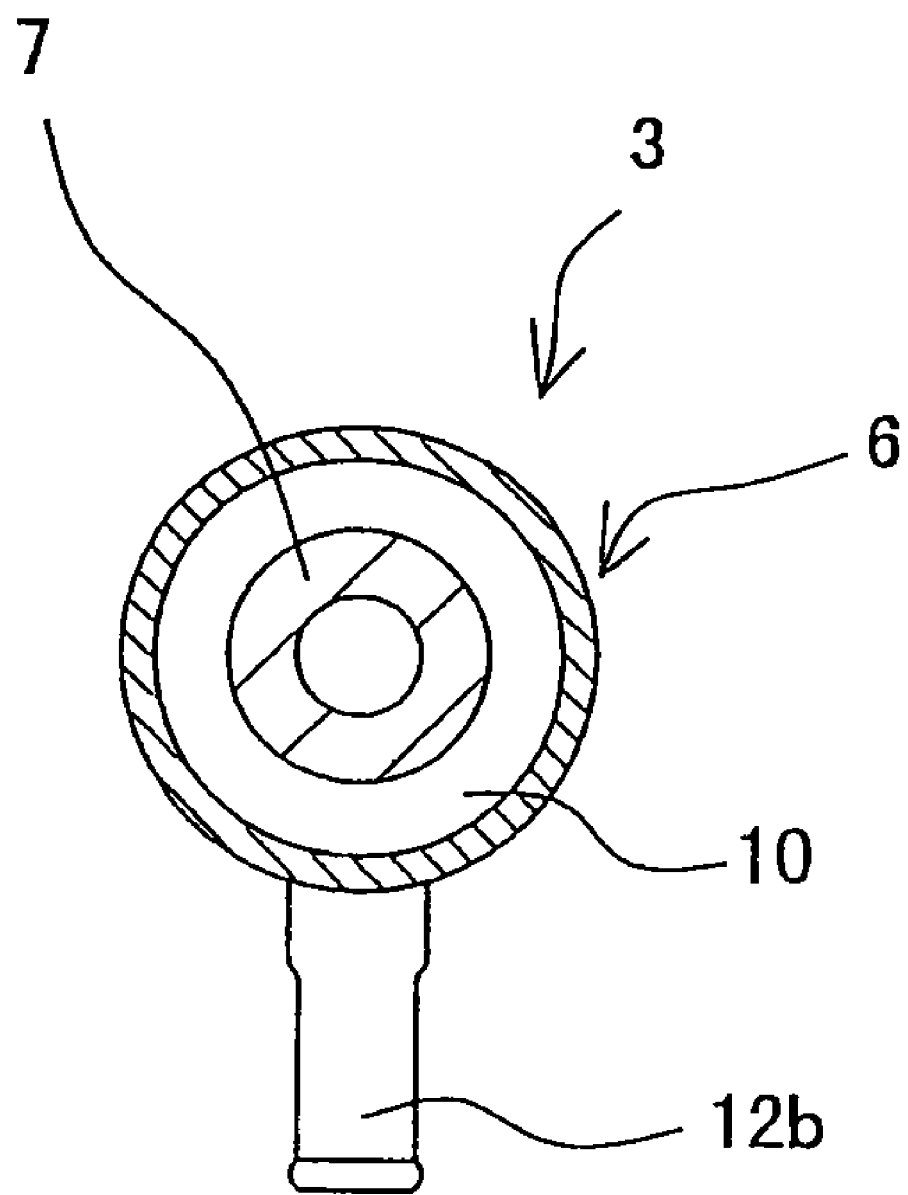
FIG. 4 is a IV-IV cross-sectional view of FIG. 2.

Referring to FIG. 2, FIG. 3 and FIG. 4, details of the collector 3 will be explained. In the figures, the collector 3 is provided mainly of a holder (one example of container) 6, a collecting filter 7 (one embodiment of filter for collecting chlorinated organic compound according to the present invention) for capturing and collecting a chlorinated organic compound contained in a sample gas, which is arranged in the holder 6, an introducing tube 8 (one example of transportation tube) for introducing the sample gas transported via the collecting tube 2 into the collecting filter 7 and a fitter 9 for fitting the introducing tube 8 to the holder 6.

The holder 6 is a generally cylindrical container made of a transparent glass, and has mainly a body 10 which can accommodate a collecting filter 7, a fitting portion 11 into which the fitter 9 is fitted, and a discharging portion 12 for discharging the sample gas.

The fitting portion 11 is disposed integrally at an end portion of the body 10, and its diameter is smaller as compared with the body 10. This fitting portion 11 has a thread groove 11a on its outer circumferential surface, and has an opening 11b at its end.

The discharging portion 12 is disposed integrally at other end of the body 10, and has a discharging path (one example of outlet) 12a for discharging the sample gas to the outside, and a branch path 12b. The branch path 12b is for inserting a temperature-measuring instrument 27 (FIG. 1) such as a thermometer and a thermocouple for measuring a temperature of the sample gas flowing in the discharging portion 12, into the discharging portion 12.

The collecting filter 7 is a cylindrical porous molded body having one closed end and an opening 7a for introducing a sample gas at other end, that is, a porous cylindrical filter. The closed end side of the collecting filter 7 is inserted in the body 10 of the holder 6 through the opening 11b while the opening 7a side is supported by the fitter 9. A size of the collecting filter 7 is not particularly limited, but usually a length is set to be 50 to 150 mm, an outer diameter of the end on the opening 7a side is set to be 12 to 35 mm, an outer diameter of the closed end side is set to be 10 to 30 mm, and a thickness is set to be 1 to 10 mm. The collecting filter 7 is formed into a taper shape such that an outer diameter of the closed end side is set to be smaller than an outer diameter of the end on the opening 7a. Details of the collecting filter 7 will be described later.

The introducing tube 8 is a tubular member made of a glass like the holder 6, and is detachable from the opening 7a of the collecting filter 7. That is, this introducing tube 8 has a connecting portion 13 for connecting to an end of the collecting tube 2 at its one end, and its other end is detachably inserted into the opening 7a of the collecting filter 7 through the fitter 9.

The fitter 9 has a first support 14 for supporting the collecting filter 7 in the holder 6, and a second support 15 for fitting the introducing tube 8 into the first support 14. The first support 14 is a member made of a resin or a metal, and has a hole portion 14a for supporting the opening 7a side end of the collecting filter 7. A thread groove 14b is formed on an inner circumferential surface of the hole portion 14a. The first support 14 is screwed to the thread groove 11a on a fitting portion 11 side of the holder 6 by the thread groove 14b thereof. In addition, the first support 14 has a projecting portion 16 which is projected toward a left direction in FIG. 3. The projecting portion 16 has a through hole 16a through which a tip portion of the introducing tube 8 can be inserted, and a thread groove 16b is formed on the outer circumferential surface thereof.

On the other hand, the second support 15 is a member made of a resin or a metal like the first support 14, and is formed into a lid-like shape in which a thread groove 15a is formed on the inner circumferential surface thereof. The second support 15 has a through hole 15b through which the introducing tube 8 is inserted. This second support 15 with the introducing tube 8 inserted into the through hole 15b, is screwed to the thread groove 16b of the projecting portion 16 of the first support 14 by the thread groove 15a.

The collecting filter 7 fitted into the above-described collector 3 can be removed from the holder 6. In this case, the second support 15 of the fitter 9 is removed from the first support 14, and the introducing tube 8 is pulled out of the collecting filter 7. Then, by removing the first support 14 from the holder 6, the collecting filter 7 is removed from the holder 6 while being supported by the first support 14.

The aspirator 4 is provided with an exhaust path 20 and a suction device 21. The exhaust path 20 has one end connected to the discharging path 12a of the collector 3 using a tubular joint 22, and has a condenser 23 and a trap 24 in this order from the collector 3 side. The suction device 21 is attached to other end of the exhaust path 20, and has a suction pump 21a and a gas meter 21b in this order. The suction pump 21a has a flow rate regulating function, and can be continuously used for 24 hours or longer. The gas meter 21b is for measuring a flow rate of a sample gas, and can measure a range of 10 to 40 l/min with accuracy of 0.1 l/min level.

Next, the collecting filter 7 used in the aforementioned collector 3 will be explained in detail. The collecting filter 7 is provided with a molded body of a three-dimensional network structure having a fluid-permeability (a gas-permeability in this embodiment), and a hydrophobic material retained in the molded body.

The molded body constituting the collecting filter 7 contains fibers (a group of fibers) and an inorganic binder. The fibers used herein do not substantially chemically react with various chlorinated organic compounds such as dioxins and a precursor thereof. Examples of the fibers include glass fiber, alumina fiber (particularly activated alumina fiber) and silica fiber. These fibers may be used solely or in combination of two or more types of them. A fiber diameter and a specific surface area of the fibers are not particularly limited.

An average aspect ratio (length/diameter) of this fibers is preferably 10,000 or smaller, particularly preferably 1,000 to 10,000. When the average aspect ratio of the fibers exceeds 10,000, a pressure loss is increased during collection of a sample fluid (sample gas), and there is a possibility that isokinetic suction prescribed in the aforementioned JIS Standard (JIS K 0311:1999) cannot be preformed.

On the other hand, the inorganic binder contained in this molded body has a nature of binding fibers to one another to incorporate a group of fibers and thereby impart a certain molded shape to the group of fibers. That is, the inorganic binder functions as a binder for retaining the group of fibers in a certain molded shape. In this embodiment, more specifically, the inorganic binder make the group of fibers set into the aforementioned shape of the collecting filter 7, that is, a cylindrical shape having one closed end.

An inorganic binder usable herein is not particularly limited as far as it has the aforementioned performance, and does not substantially chemically react with a chlorinated organic compound like the fibers, but an inorganic binder having an adsorbing capability, in particular, an adsorbing capability for a chlorinated organic compounds is preferable. Examples of the inorganic binder having such a adsorbing capability include alumina (in particular activated alumina), zeolite, silicon dioxide (silica), acid clay and apatite. These inorganic binders may be used solely or in combination of two or more of them. In addition, a form of the inorganic binder is not particularly limited, but usually a particulate inorganic binder is used.

Herein, zeolite is hydrous aluminosilicate represented by the general formula $X_m Y_n O_{2n} \cdot sH_2O$. In the general formula, X represents Na, Ca or K, Y represents Si+Al, and s is not constant. As such zeolite, synthetic zeolite is preferably used.

Among the aforementioned inorganic binders, in the present invention, an inorganic binder having tar-adsorbing capability is particularly preferably used. When an inorganic binder having such a characteristic is used, the collecting filter 7 can effectively adsorb a tar produced and derived from, for example, carbon monoxide contained in a sample gas (details of the tar will be described later), and can more assuredly capture and collect various chlorinated organic compounds such as dioxins dissolved in the tar. Examples of the inorganic binder which can adsorb a tar include alumina, zeolite and silicon dioxide. As the alumina, activated alumina is particularly preferably used. These inorganic binders which can adsorb a tar may be used solely or in combination of two or more of them.

A bulk density of the aforementioned molded body containing the fibers and the inorganic binder is preferably set at 0.1 to 1 g/cm³, more preferably 0.3 to 0.7 g/cm³. In the case where the bulk density of the molded body is smaller than 0.1 g/cm³, a part of chlorinated organic compounds contained in a sample gas is passed through the collecting filter 7 in some cases, and it becomes difficult to collect chlorinated organic compounds contained in the sample gas without substantial leakage, in some cases. Conversely, in the case where the bulk density exceeds 1 g/cm³, in the collecting filter 7, when a particulate substance contained in a sample gas is captured, a pressure loss may be increased, and there is a possibility that the sample gas hardly passes therethrough. As a result, there is a possibility that it becomes difficult to perform isokinetic suction prescribed in the aforementioned JIS Standard (JIS K 0311:1999), in the collecting filter 7. In addition, in an extraction procedure described later for extracting the chlorinated organic compounds collected by the collecting filter 7, an extraction rate may be reduced.

On the other hand, the hydrophobic material retained in the aforementioned molded body does not substantially chemically react with a chlorinated organic compound. The hydrophobic material is not particularly limited as far as it has higher hydrophobicity than that of the aforementioned fibers and inorganic binder, but a hydrophobic material having an adsorbing capability, in particular, adsorbing capability for a chlorinated organic compound is preferable. As the hydrophobic material having such an adsorbing capability, at least one kind selected from the group consisting of, for example, activated carbon, graphite and styrene-divinylbenzene copolymer (e.g. trade name "XAD-2" of Sigma-Aldrich Corporation in U.S.A.) is preferable. Alternatively, as the hydrophobic material, a material having an alkylsilyl group, for example, a material having an alkylsilyl group having 8 to 18 carbon atoms may be used. Further, a form of the hydrophobic material is not particularly limited, but usually a powdery or particulate hydrophobic material is used.

It is preferable that the hydrophobic material is retained at usually 0.01 to 10.0% by weight, preferably 0.05 to 5.0% by weight of the molded body. In the case where an amount of the hydrophobic material is smaller than 0.01% by weight, there is a possibility that it becomes difficult to collect chlorinated organic compounds contained in a sample gas using the collecting filter 7 without substantial leakage if the sample gas contains a large amount of water. Conversely, in the case where an amount of the hydrophobic material exceeds 10.0% by weight, in the collecting filter 7, there is a possibility that a pressure loss is increased when a particulate substance contained in a sample gas is captured, and the sample gas hardly passes therethrough. As a result, there is a possibility that it becomes difficult to perform isokinetic suction prescribed in the aforementioned JIS Standard (JIS K 0311:1999), in the collecting filter 7. In addition, in an extraction procedure described later for extracting chlorinated organic compounds collected by the collecting filter 7, the extraction may become difficult, leading to reduction in an extraction rate.

A preferable collecting filter 7 is such that powdery activated carbon as the hydrophobic material is retained in the molded body using activated alumina fibers as the fibers and particulate activated alumina as the inorganic binder. In particular, the molded body having a bulk density in a range of 0.3 to 0.7 g/cm$^3$ is most preferable.

The aforementioned collecting filter 7 can be usually prepared by preparing the aforementioned molded body, and making this molded body retain the hydrophobic material. Specifically, the filter can be prepared as follows:

First, a molding material containing the aforementioned fibers and inorganic binder is prepared. Herein, a dispersion in which an inorganic binder is dispersed in water is prepared, then fibers are added to this dispersion to uniformly mix the inorganic binder and the fibers. Thereupon, it is preferable that a ratio of mixing the fibers and the inorganic binder is such that a bulk density of the desired molded body is appropriately adjusted to be in the aforementioned range.

Then, the resulting molding material is molded in a predetermined shape, that is, a cylinder having one closed end, to obtain a molded body. As a molding method herein, well known various molding methods such as a wet die molding method can be adopted. Next, the resulting molded body is thermally treated to sinter to obtain the desired molded body. A temperature at the time of sintering is not particularly limited, but when alumina is used for either one or both of the fibers and the inorganic binder, the temperature is preferably set in a range in which the alumina can be activated and converted into activated alumina, specifically, at 150 to 700° C.

The thus prepared molded body may further be immersed into an aqueous dispersion in which an inorganic binder is dispersed in water, and then subjected to drying treatment. When the molded body is subjected to such treatment, the molded body is impregnated with an inorganic binder, and a molded body containing a larger amount of the inorganic binder can be prepared. In addition, by way of such treatment, the bulk density of the molded body can be adjusted in the aforementioned preferable range. Since such a molded body consequently contains a large amount of the inorganic binder, when an inorganic binder having the aforementioned tar adsorbing capability is used, chlorinated organic compounds contained in a sample gas can be effectively captured without leakage even when hydrocarbons or carbon monoxide as an unburnt substance described later is contained at a large amount in the sample gas. A method of drying the molded body is not particularly limited, but usually it is preferable to adopt a method of heat-treating the molded body at around 150 to 700° C. to remove water.

Next, the resulting molded body is made to retain a hydrophobic material. A method for doing so is not particularly limited, but for example, there is a method of making the molded body retain a hydrophobic material using the aforementioned holder 6. In this method, the molded body obtained in the aforementioned step is charged into the holder 6 and the branch path 12b is closed, and then a suction device such as a suction pump is connected to the discharging path 12a side. Subsequently, the suction device is operated to suck the interior of the holder 6 and, at the same time, a hydrophobic material is supplied into an introducing tube 8. Thereby, the hydrophobic material supplied into the introducing tube 8 is sucked in a direction toward the molded body, and is retained mainly in a direction of the inner circumferential side to the thickness direction of the molded body. Thereupon, it is preferable that an amount of the hydrophobic material to be supplied from the introducing tube 8 is set so that a ratio relative to the molded body is in the aforementioned range.

Then, a method of using the aforementioned collecting apparatus 1, that is, a method of collecting a chlorinated organic compound using the aforementioned collecting apparatus 1 will be explained. Herein, the case where a sample gas is collected from an exhaust gas flowing in a space, for example in a flue, of an incineration facility for incinerating wastes and various chlorinated organic compounds such as dioxins contained in the sample gas are collected, will be explained. In this case, as shown in FIG. 1, the tip portion of the collecting tube 2 of the collecting apparatus 1 is inserted into a flue 25 through a sample collecting port 25a disposed in the flue 25. Thereupon, a packing 26 is attached to the collecting tube 2 to air-tightly seal the gap between the collecting tube 2 and the sample collecting port 25a. In addition, a temperature-measuring instrument 27 such as a thermometer and a thermocouple is fitted into the branch path 12b of the collector 3.

In this state, the suction pump 21a is operated to carry out isokinetic suction of a part of exhaust gas flowing in the flue 25 as a sample gas into the collecting tube 2. Thereupon, it is preferable that a temperature, a flow rate, a pressure and an amount of water of the exhaust gas flowing in the flue 25 are measured to calculate an isokinetic suction amount according to, for example, JIS Z 8808 and, based on the calculation result, a suction flow rate by the suction pump 21a is adjusted. It is preferable that the flow rate set herein is appropriately regulated so that the result is appropriately monitored with the gas meter 21b, and the isokinetic suction state is continued.

A sample gas which has flown into the collecting tube 2 is cooled by the cooling device 5, and is usually cooled to a temperature of a dioxins production temperature or lower, for example, a temperature of 120° C. or lower. Thereby, in the collecting tube 2, new generation of dioxins is prevented.

The cooled sample gas is flown into the collecting filter 7 from the collecting tube 2 via the introducing tube 8 of the collector 3. The sample gas which has been flown into the collecting filter 7 passes through the collecting filter 7, and then is flown into the body 10 of the holder 6 and, further, is flown toward the aspirator 4 via the discharging path 12a as indicated by arrows in FIG. 3. Thereupon, various dusts, as well as various chlorinated organic compounds such as dioxins in both particulate form and gaseous form contained in the sample gas are captured at the same time by the aforementioned fibers and inorganic binder contained in the molded body constituting the collecting filter 7 and by the hydrophobic material, and are collected from the sample gas.

Meanwhile, when a carbon compound such as unburnt hydrocarbons and carbon monoxide (CO) is contained at a large amount in a sample gas, a tar derived from the carbon compound is easily produced in the sample gas. In many cases, the tar dissolves various chlorinated organic compounds including dioxins therein and takes them inside. For this reason, when a collecting filter 7 not using an inorganic binder having tar adsorbing capability, for example, a collecting filter composed of a molded body obtained by molding the aforementioned fibers using an organic binder such as a cellulose binder is used, the filter can not effectively capture a tar produced in the sample gas, and consequently there is a possibility that a part of tar contained in the sample gas passes through the filter and is discharged to the outside. That is, there is a possibility that the part of tar and chlorinated organic compounds dissolved therein are discharged to the outside without being collected by the filter. This is a phenomenon that the present inventors found out during a process to the present invention. It has been also found that, when an amount of an unburnt carbon compound is determined using carbon monoxide as an index, in particular, if the concentration of carbon monoxide contained in a sample gas exceeds 150 ppm, such a passage of tar can occur remarkably.

To the contrary, the collecting filter 7 in accordance with this embodiment, when the filter is composed of a molded body containing the aforementioned fibers and inorganic binder having tar adsorbing capability, can capture also a tar contained in a sample gas substantially without leakage, even if the concentration of an unburnt carbon compound in the sample gas is high (for example, even if the concentration of carbon monoxide in the sample gas exceeds 150 ppm). That is, whether the concentration of an unburnt carbon compound in a sample gas is high or low, this collecting filter 7 can capture and collect various chlorinated organic compounds such as dioxins in both particulate form and gaseous form contained in the sample gas substantially without leakage.

In addition, when rapidly cooled by spraying water in the flue 25, a sample gas has an increased amount of water in some cases. However, even in such a case, since the collecting filter 7 contains the aforementioned hydrophobic material, it can capture and collect various chlorinated organic compounds such as dioxins in both particulate form and gaseous form contained in the sample gas substantially without leakage.

As described above, the sample gas from which dusts as well as various chlorinated organic compounds in particulate form and gaseous form have been selected by the collecting filter 7 substantially without leakage, is subsequently flown from the discharging path 12a toward the aspirator 4. Thereupon, a temperature of the sample gas flowing in the discharging path 12a is measured and managed by the temperature-measuring instrument 27 fitted in the branch path 12b.

The sample gas discharged from the discharging path 12a is flown into the exhaust path 20, and is further cooled with the condenser 23. Thereby, the moisture contained in the sample gas is condensed, and is stored in the trap 24. The sample gas from which the moisture has been removed like this is discharged to the outside from the gas mater 21b via the suction pump 21a. Collection of a sample gas, that is, an exhaust gas with such a collecting apparatus 1 is usually preformed for a time corresponding to an amount of the exhaust gas presumed from a detection limit value of the chlorinated organic compounds (usually, an exhaust gas of 1 to 3 $Nm^3/3$ to 4 hours).

When the concentration of a chlorinated organic compound contained in the thus collected sample gas (exhaust gas) is analyzed, the collecting apparatus 1 is removed from the flue 25, and the collector 3 is separated from the collecting apparatus 1. Further, the collecting filter 7 is removed from the separated collector 3.

Then, the interiors of the collecting tube 2, the introducing tube 8 and the holder 6 are washed using a solvent, and a washing solution thereupon is maintained. In addition, chlorinated organic compounds captured by the collecting filter 7 of the collector 3 are extracted with a solvent. Herein, a procedure for extracting chlorinated organic compounds captured by the collecting filter 7 can be performed using, for example, a conventional Soxhlet's extractor. Alternatively, when this collecting filter 7 is set to be a miniature size as described above, since it can be accommodated in a high speed extractor cell, the extraction procedure can be rapidly performed using the high speed extractor.

When a bulk density of a molded body constituting the collecting filter 7 is set in the aforementioned range and, a content of the hydrophobic material is set in the aforementioned range, it is not necessary to set special extraction condition for shortening an extraction time, and captured chlorinated organic compounds can be rapidly dissolved in a solvent in a short time.

Upon analysis of chlorinated organic compounds, the aforementioned washing solution and the extract obtained by the aforementioned extraction procedure are combined, and this is subjected to an analysis procedure. As an analysis method in this case, a method using a gas chromatographic mass spectroscopy (GC/MS method) can be adopted according to a method described in "Standard Measurement and Analysis Manual For Dioxins In Waste Treatment" (published in March, 1997 by Japan Waste Research Foundation) edited by Japanese Ministry of Health and Welfare, Environmental Health Bureau, Water Supply and Environmental Sanitation Department, Environmental Maintenance Section, or a method prescribed in Japanese Industrial Standard JIS K 0311:1999 (established on Sep. 20, 1999).

When another sample gas is collected using the collecting apparatus 1, for example, the collector 3 is replaced with a new one. In this case, since the collecting apparatus 1 can be used for collecting a next sample gas by sufficiently washing only the collecting tube 2, the preparatory work before sample gas collection is considerably alleviated as compared with that carried out using conventional impingers. As a result, a necessary time for collecting a sample gas can be considerably shortened, and also a necessary cost for collecting a sample gas can be considerably reduced, as compared with those using conventional impingers. In addition, since this collecting apparatus 1, in particular, the collector 3 has a simple construction as compared with a conventional complicated collecting apparatus, so that it is easy to handle and transport. For this reason, when this collecting apparatus 1 is used, a work of collecting a sample gas can be easily performed even on a flue in which a conventional large scale collecting apparatus using impingers is difficult to be disposed.

The once used collector 3 can be reused repeatedly when the holder 6 and the introducing tube 8 are sufficiently washed, and the collecting filter 7 is replaced with a new one.

The aforementioned embodiment can be modified, for example, as follows:

(1) Although a cylindrical filter is used as the collecting filter 7 in the aforementioned embodiment, the present invention is not limited to this. For example, the present invention can be carried out in the same manner in the case the collecting filter 7 is formed into a column-like or a disk-like shape.

(2) Although the case where a chlorinated organic compound such as dioxins contained in an exhaust gas (a sample gas) discharged from an incinerator for wastes is collected was explained in the aforementioned embodiment, the collecting filter, the collector and the collecting method of the present invention can be similarly utilized also in the case where a chlorinated organic compound in a fluid other than an exhaust gas is collected. For example, the collecting filter and the like of the present invention can be similarly utilized also when a chlorinated organic compound contained in an environmental air, as well as a chlorinated organic compound contained in water such as factory waste-water, sea water, fresh water and tap water and the like are collected.

When a chlorinated organic compound contained in water such as factory waste-water is collected, a sample to be collected is a liquid sample. In this case, there is a possibility that the liquid sample contains various chlorinated organic compounds in various states such as a particulate state, a foam state (that is, air-liquid mixed state) and a dissolved state (that is, dissolved in water state), but the collecting filter of the present invention can capture and collect various chlorinated organic compounds in such various states at the same time from the liquid sample.

EXAMPLE

An alumina dispersion in water containing about 20% by weight of particulate alumina (inorganic binder) was prepared, and alumina fibers (containing 72% by weight of γ-alumina and 28% by weight of silica) having an average fiber diameter of 6 μm and an average aspect ratio of 2,000 as fibers were added to this alumina dispersion in water to mix them. The resulting molding material was molded into a cylinder having one closed end, and sintered at 200° C. Thereby, a cylindrical molded body having air permeability of a weight of 8.5 g and a bulk density of 0.38 g/cm$^3$ was obtained in which the outer diameter of the opening end side was set to be 19 mm, the outer diameter of the closed end side was set to be 18 mm, the thickness was set to be 5 mm and the length was set to be 120 mm, respectively. The alumina fibers and the particulate alumina contained in this molded body were 5.7 g and 2.8 g, respectively.

Figure 5:
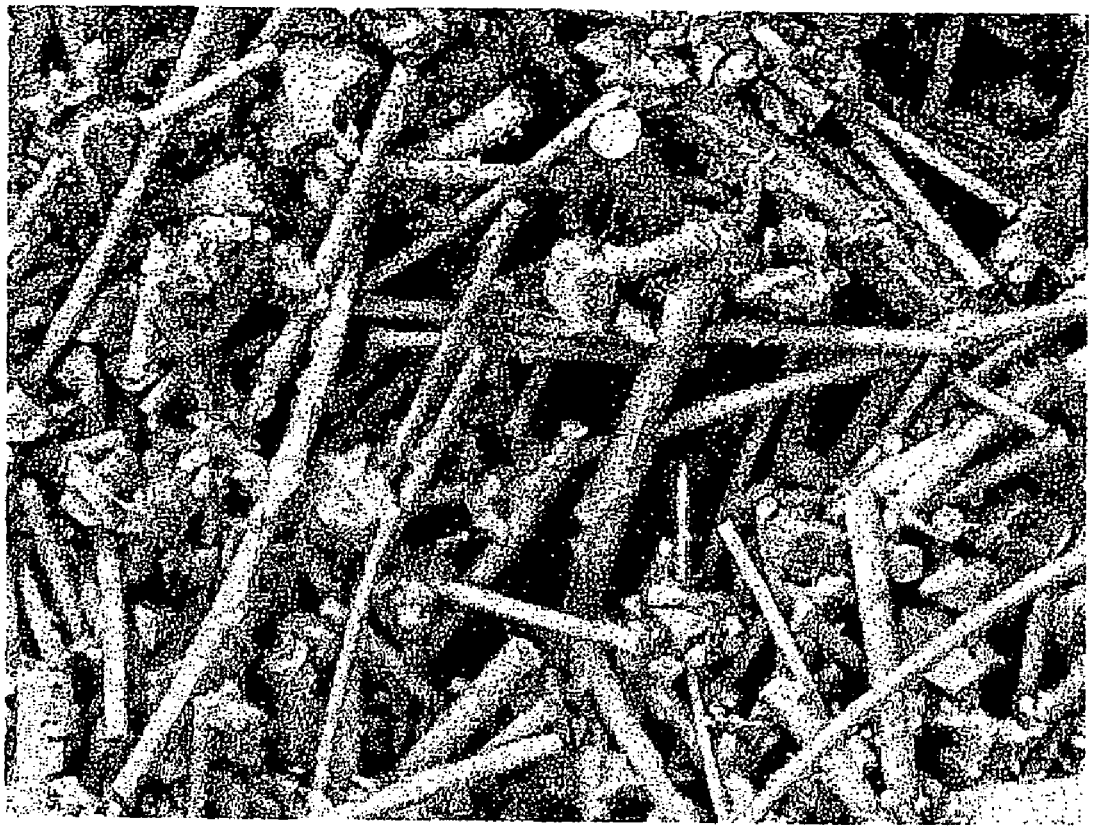
FIG. 5 is an electron microscopic photograph of a part of the molded body obtained in Example.

An electron microscopic photograph of a part of the resulting molded body is shown in FIG. 5. From FIG. 5, it is seen that this molded body has a fine network structure (three-dimensional network structure) having air permeability, which was formed by binding of alumina fibers with particulate alumina as an inorganic binder.

Next, the resulting molded body was further immersed in a dispersion in water in which particulate alumina was dispersed at 20% by weight, and then taken out and dried by heat-treating at 200° C. Thereby, a molded body having a weight of 12.8 g and a bulk density 0.6 g/cm$^3$ was obtained.

The resulting molded body was used in place of the collecting filter 7 to prepare the collector 3 relating to the aforementioned embodiment, and the branch path 12b of the collector 3 was closed to connect the suction pump to the discharging path 12a side. The suction pump was operated to suck the interior of the holder 6 and, at the same time, powdery activated carbon (trade name "Kuraray Coal PK-DN" manufactured by Kuraray Chemical Co., Ltd.) was introduced into the introducing tube 8. Thereby, 12 mg of powdery activated carbon was retained mainly from the inner circumferential side to the thickness direction of the molded body, to obtain the collecting filter 7.

Figure 6:
FIG. 6 is an electron microscopic photograph of a part of the collecting filter obtained in Example.

An electron microscopic photograph of a part of the resulting collecting filter 7 is shown in FIG. 6. From FIG. 6, it is seen that this collecting filter 7 has a structure in which powdery activated carbon is retained mainly on the inner circumferential side of the aforementioned molded body.

Using the resulting collecting filter 7, the collector 3 for a chlorinated organic compound relating to the aforementioned embodiment was made, and this collector 3 was used to construct the collecting apparatus 1 relating to the aforementioned embodiment. This collecting apparatus 1 was used to collect several kinds of sample gases (exhaust gases) having different amounts of water and average carbon monoxide concentrations from a flue of an incinerator during incineration-treatment of wastes, and various chlorinated organic compounds such as dioxins contained in each of the sample gases were collected. Thereupon, a sample gas collecting apparatus provided with an impinger exemplified in JIS K 0311:1999 (hereinafter, referred to as "JIS-exemplified apparatus") was connected to the later stage of the collecting apparatus 1, so that the sample gas which had passed through the collecting apparatus 1 was discharged after passed through the JIS-exemplified apparatus. The aforementioned amount of water is a ratio (volume percentage (%)) of water steam contained in an exhaust gas, and is prescribed in JIS Z 8808:1995 (established on Mar. 1, 1995) "Method of Measuring Dust Concentration in Flue Gas". Conditions of collecting the sample gases were according to conditions prescribed in JIS K 0311:1999.

Figure 7:
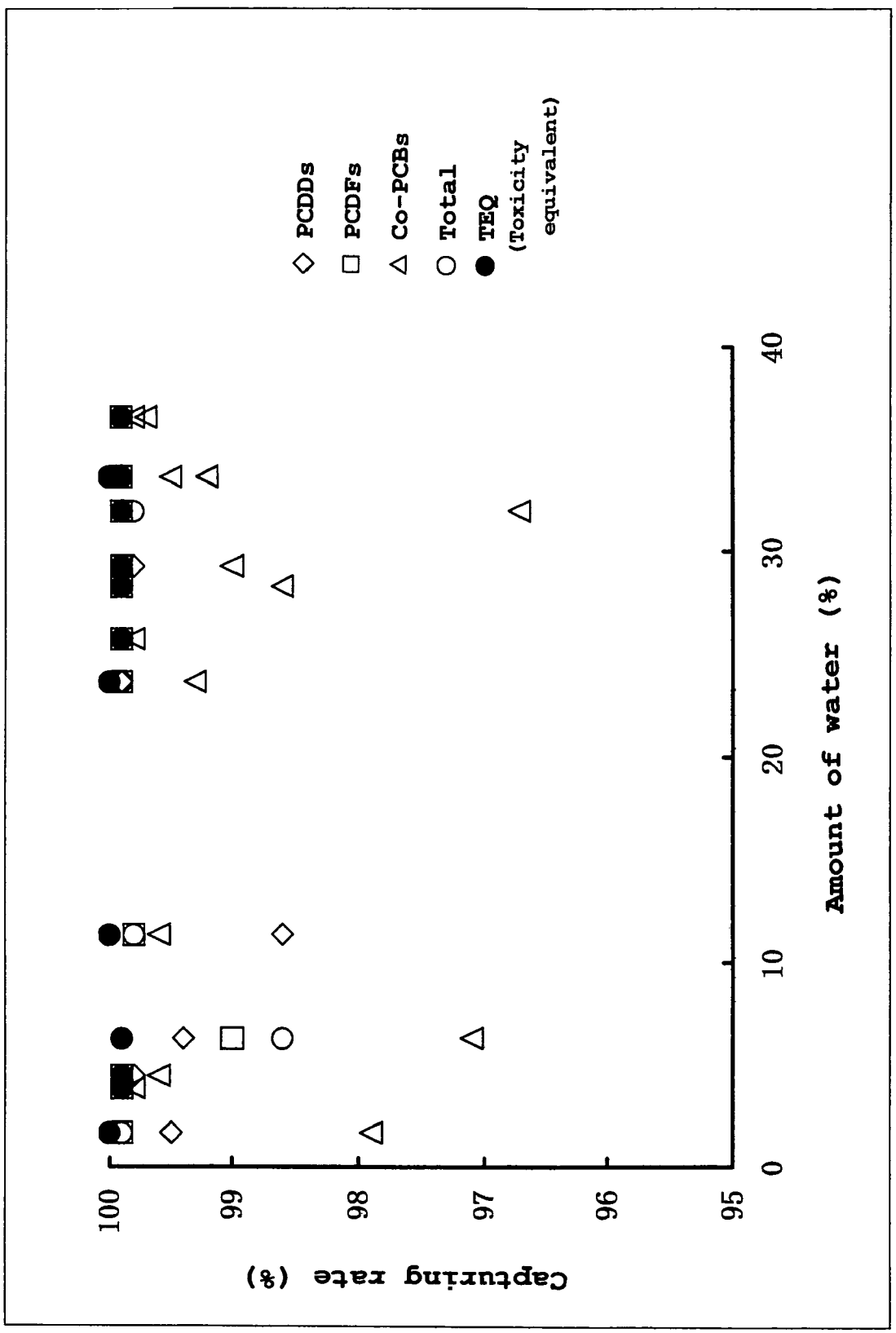
FIG. 7 is a graph showing results of investigation of relationship between an amount of water in a sample gas and a capturing rate in Example.
Figure 8:
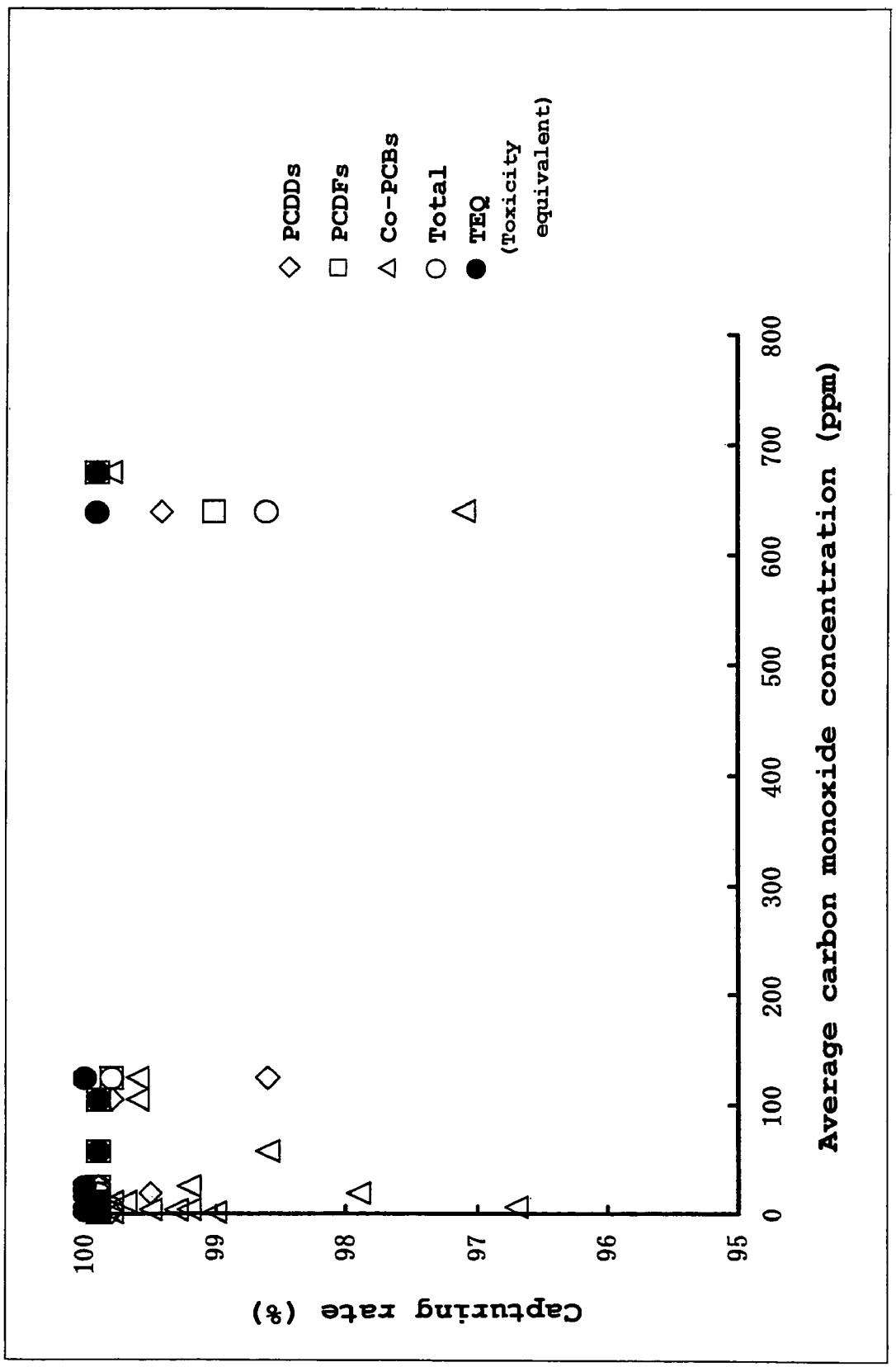
FIG. 8 is a graph showing results of investigation of relationship between an average carbon monoxide concentration in a sample gas and a capturing rate in Example.

Chlorinated organic compounds collected by the collecting apparatus 1 and the JIS-exemplified apparatus, respectively, were extracted by the method according to JIS K 0311:1999, and quantitatively analyzed according to the analysis method prescribed in the same JIS. Then, an amount of chlorinated organic compounds (A) collected by the collecting apparatus 1 and an amount of chlorinated organic compounds (B) collected by the JIS-exemplified apparatus were obtained, respectively, and a capturing rate (%) of chlorinated organic compounds collected by the collecting apparatus 1 was obtained according to the following equation. The results are shown in FIG. 7 and FIG. 8. FIG. 7 shows the relationship between an amount of water of the sample gas and a capturing rate, and FIG. 8 shows the relationship between an average carbon monoxide concentration of the sample gas and a capturing rate.

$$\text{Capturing rate } (\%) = A/(A+B) \times 100$$

From FIG. 7 and FIG. 8, it is seen that since the collecting apparatus 1 is provided with the aforementioned collecting filter 7, it can collect various chlorinated organic compounds including dioxins in both particulate form and gaseous form contained in the sample gases substantially without leakage, whether an average carbon monoxide concentration in a sample gas is high or low (that is, although a concentration of an unburnt carbon compound in a sample gas is high) and whether an amount of water in a sample gas is large or small.

INDUSTRIAL APPLICABILITY

Since a filter for collecting chlorinated organic compound of the present invention is provided with a molded body containing fibers and an inorganic binder, and a hydrophobic material having higher hydrophobicity than that of the fibers and the inorganic binder, which is retained in the molded body, it can capture and collect various chlorinated organic compounds including dioxins in both particulate form and gaseous form contained in a fluid at the same time. In addition, the collected chlorinated organic compounds can be easily extracted from the filter.

The present invention can be practiced in other various forms without departing from a spirit and main features thereof. Therefore, the aforementioned embodiments or example are merely an example in all respects, and are not to be interpreted as limitation. A scope of the present invention is indicated by claims, and is not restricted by the text of the specification at all. Further, variations and modifications belonging to an equivalent scope of claims are all within the scope of the present invention.

The invention claimed is:

1. A filter for selecting and collecting a chlorinated organic compound contained in a fluid from the fluid, comprising:
    a fluid-permeable cylindrical molded body having one closed end and containing fibers and an inorganic binder for binding the fibers to one another, and
    a hydrophobic material having higher hydrophobicity than that of the fibers and the inorganic binder, which is retained in the molded body,
    wherein the hydrophobic material is retained mainly in a direction of the inner circumferential side to the thickness direction of the molded body.

2. The filter according to claim 1, wherein the fibers are at least one kind of fibers selected from a group consisting of glass fiber, alumina fiber and silica fiber.

3. The filter according to claim 1, wherein the fibers have an average aspect ratio of 1,000 to 10,000.

4. The filter according to claim 1, wherein the inorganic binder has adsorbing capability for the chlorinated organic compound.

5. The filter according to claim 1, wherein the inorganic binder has adsorbing capability for a tar.

6. The filter according to claim 1, wherein the inorganic binder is at least one selected from a group consisting of alumina, zeolite and silicon dioxide.

7. The filter according to claim 1, wherein the inorganic binder is particulate.

8. The filter according to claim 1, wherein the hydrophobic material has adsorbing capability for the chlorinated organic compound.

9. The filter according to claim 8, wherein the hydrophobic material is at least one kind selected from the group consisting of active carbon, graphite and styrene-divinylbenzene copolymer.

10. The filter according to claim 1, wherein a bulk density of the molded body is 0.1 to 1 g/cm$^3$.

11. The filter according to claim 1, wherein the hydrophobic material is retained at 0.01 to 10.0% by weight of the molded body.

12. The filter according to claim 1, wherein the fibers are activated alumina fibers, the inorganic binder is particulate activated alumina and the hydrophobic material is powdery activated carbon.

13. The filter according to claim 12, wherein a bulk density of the molded body is 0.3 to 0.7 g/cm$^3$.

14. A process for producing a filter for selecting and collecting a chlorinated organic compound contained in a fluid, from the fluid, comprising steps of:
preparing a molding material containing fibers and an inorganic binder for binding the fibers to one another,
molding the molding material into a cylinder having one closed end and sintering this to obtain a molded body, and
making the molded body retain a hydrophobic material having higher hydrophobicity than that of the fibers and the inorganic binder so that the hydrophobic material is retained mainly in a direction of the inner circumferential side to the thickness direction of the molded body.

15. The process for producing a filter according to claim 14, wherein at least one of the elements including the fibers and the inorganic binder is alumina, and a temperature at sintering is set at 150 to 170° C.

16. The process for producing a filter according to claim 14, which further comprises a step of immersing the molded body with an aqueous dispersion of the inorganic binder and then drying the body, before the step of making the molded body retain the hydrophobic material.

17. A collector for collecting a chlorinated organic compound contained in a fluid flowing in a transportation tube, comprising:
a fluid-permeable filter for passing the fluid from the transportation tube, and
a container for accommodating the filter, and having an outlet for discharging to the outside the fluid which has passed through the filter,
wherein the filter is provided with a cylindrical molded body having an opening for inserting the transportation tube into one side and closed in the other side and containing fibers and an inorganic binder for binding the fibers to one another, and a hydrophobic material having higher hydrophobicity than that of the fibers and the inorganic binder, which is retained mainly in a direction of the inner circumferential side to the thickness of the molded body.

18. A method for collecting a chlorinated organic compound contained in a fluid flowing in a transportation tube, comprising a step of:
passing the fluid from the transportation tube through a filter provided with a fluid-permeable cylindrical molded body having an opening for inserting the transportation tube into one side and closed in the other side and containing fibers and an inorganic binder for binding the fibers to one another, and a hydrophobic material having higher hydrophobicity than that of the fibers and the inorganic binder, which is retained mainly in a direction of the inner circumferential side to the thickness direction of the molded body.

* * * * *